United States Patent [19]

Eberhard et al.

[11] E Re. 31,440

[45] Reissued Nov. 15, 1983

[54] ELECTROCHEMICAL ELECTRODE WITH HEATING MEANS

[75] Inventors: Patrick Eberhard, Allschwil, Switzerland; Konrad Hammacher, Tübingen, Fed. Rep. of Germany; Wolfgang Mindt, Reinach, Switzerland

[73] Assignee: Hoffmann-La Roche Inc., Nutley, N.J.

[21] Appl. No.: 870,392

[22] Filed: Jan. 18, 1978

Related U.S. Patent Documents

Reissue of:

[64] Patent No.: 3,795,239
Issued: Mar. 5, 1974
Appl. No.: 177,231
Filed: Sep. 2, 1971

[30] Foreign Application Priority Data

Oct. 1, 1970 [CH] Switzerland ..... 14544/70

[51] Int. Cl.[3] ..... A61B 5/00

[52] U.S. Cl. ..... 128/635; 204/403; 204/406

[58] Field of Search ..... 128/2 E, 21 E, 399, 128/303.1, 635; 324/30 R; 204/195 B, 195 P

[56] References Cited

U.S. PATENT DOCUMENTS

| | | | |
|---|---|---|---|
| 2,886,771 | 5/1959 | Vincent | 128/2 E X |
| 3,000,805 | 9/1961 | Carritt et al. | 128/2 E X |
| 3,325,378 | 6/1967 | Greene et al. | 204/195 P X |
| 3,357,910 | 12/1967 | Shiller | 128/2.1 E X |
| 3,468,781 | 9/1969 | Lucero | 204/195 P |
| 3,507,283 | 4/1970 | Thomas, Jr. | 128/303.1 |
| 3,659,586 | 5/1972 | Johns et al. | 128/2 E |
| 3,664,178 | 5/1972 | Spergel et al. | 73/53 |

FOREIGN PATENT DOCUMENTS

| | | | |
|---|---|---|---|
| 1128226 | 9/1968 | United Kingdom | 128/635 |
| 172110 | 7/1965 | U.S.S.R. | 128/635 |

OTHER PUBLICATIONS

Davies, P. W. et al., *Rev. Scient. Instr.*, vol. 13, 524–533, (1942).
Baumberger, J. P. et al., *Amer. Physiol. Soc. Fed. Proceed., vol. 10, pp. 10–11, (1951).*
Rooth, G. et al, *Science Tools–The LKB Instr. J.*, vol. 4, No. 3, pp. 37–42, (1957).
Bolie, V. W., *I.R.E. Trans. on Med. Electronics*, vol. 7, No. 4, pp. 330–333, (1960).
Severinghaus, J. W., *Anesthesiology*, vol. 21, No. 6, pp. 717–726, (1960).
Silver, I. A., *A Symp. on Oxy. Meas. in Blood & Tissues & Their Significance*, J. P. Payne et al., London, 1966, pp. 135–153.
Silver, I. A., *Phys. Med. Biol.*, vol. 12, No. 3, pp. 285–299 (1967).
*J.A.M.A.*, vol. 205, No. 4, pp. 19–20, (1968).
Evans, N. T. S., et al., *Progr. Resp. Res.*, vol. 3, pp. 161–164 (1969).
Huch, A. et al., *Arch. Gynak.*, 207:443–451, (1969).
Lucero, D. P., *Anal. Chem.*, 41, No. 4, Apr. 1969, pp. 613–622.
Evans, N. T. S. et al., *Respiration Physiology*, (1967) 3, 21∝37.
Naylor, P. F. D. et al., *Br. J. Derm.*, (1968) 80, 643–651.

*Primary Examiner*—Kyle L. Howell
*Attorney, Agent, or Firm*—Jon S. Saxe; Bernard S. Leon; George W. Johnston

[57] ABSTRACT

An electrode arrangement for application to a body surface for bloodless measurement in connection with the concentration or the partial pressure of a gas in the blood comprising a sensor unit having a face member for body contact, and a heating unit coupled to the sensor unit for transmitting to said face member a thermal condition for thermal stimulation of the local blood circulation. In a further embodiment, the sensor unit includes at the face member a cover membrane permeable for a gas to be measured.

8 Claims, 3 Drawing Figures

ELECTROCHEMICAL ELECTRODE WITH HEATING MEANS

Matter enclosed in heavy brackets [ ] appears in the original patent but forms no part of this reissue specification; matter printed in italics indicates the additions made by reissue.

BACKGROUND OF THE INVENTION

1. Field of the Invention

The invention is concerned with an electrode arrangement suitable for bloodless measurements in connection with the concentration or the partial pressure of a gas in the blood.

2. Description of the Prior Art

It is known to bloodlessly measure the partial pressure of a gas in the blood (e.g. of oxygen or $CO_2$) with electrodes. Generally, an electrode is applied to a position of the body surface of the patient, for example the scalp, a wrist, the inner canthus of an eye, etc. With the presence of an initial potential at the electrode, an electrochemical reaction takes place at its surface, whereby gas is diffused through the tissue from the blood (e.g. in the case of oxygen, its reduction to $OH^-$ ions). The resulting current is measurable and under certain circumstances is proportional to the concentration or the partial pressure of the gas in the blood.

Bare electrodes or electrodes covered with a membrane are suitable, depending on the particular measurement requirements, and platinum is preferred for the electrode material. Typical materials for the membrane material would include polypropylene, polyethylene, teflon, mylar, etc.

It has been found that the measured current values derived by the electrodes are not only a function of the actual partial pressure of a gas in the blood, but, in addition, depend on the local blood circulation of the tissue in the electrode measuring region. Because of the latter, for some measurements, it would be advantageous to decrease the influence of the blood circulation on the measuring results by hyperaemising the skin in the measuring region to increase the blood volume. It has already been proposed to use suitable vasodilating preparations (for example, histamine, papaverine, nicotinic acid, etc.) for this purpose. However, the application of such preparations is problematical in certain cases, for example, in the case of measurement on the inner canthus of the eye.

SUMMARY OF THE INVENTION

Accordingly, it is the purpose of the present invention to provide an electrode arrangement in which the local blood circulation and thus the blood volume in the measuring region of the electrode is increased to enhance the transport of gas from the blood and also the system response time, without additional application of hyperaemising preparations. This is achieved by providing an electrode arrangement with a heater for the thermal stimulation of local blood circulation.

DESCRIPTION OF THE PREFERRED EMBODIMENT

Figure 1:
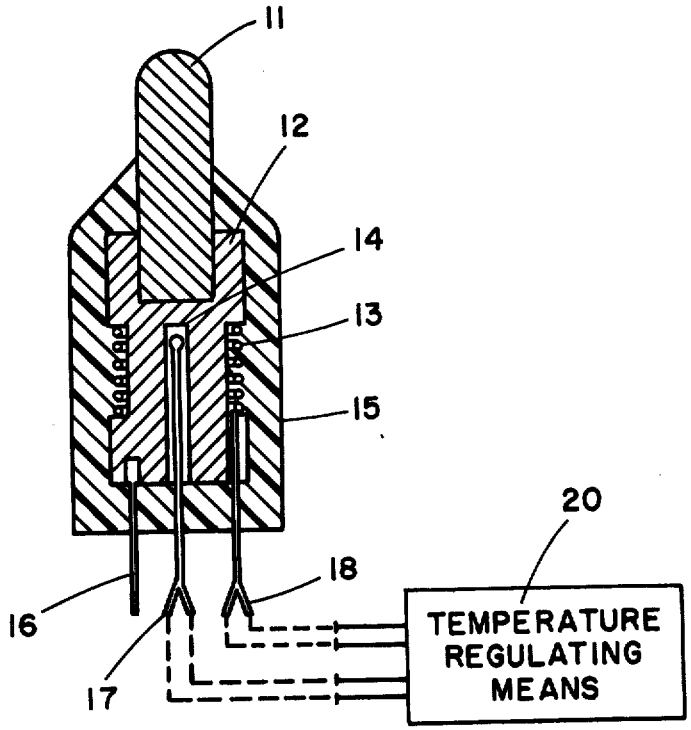
FIG. 1 shows a longitudinal section through one embodiment of an electrode arrangement according to the invention, with a bare electrode for detecting a substance (for example, a gas) dissolved in the blood.

The electrode arrangement shown in FIG. 1 is particularly suitable for detecting at the inner canthus of an eye, a gas (for example, hydrogen) transported by the circulation. With it one may measure, for example, the transport time of an inhaled gas in the blood pathway from the lung to the inner canthus.

A platinum electrode 11 serves as the contact medium with the skin of the inner canthus of an eye. Its configuration is generally cylindrical with a approximately 3 mm diameter and a spherically rounded-off contact or application surface at the tip which proves to be quite advantageous for this purpose. The platinum electrode 11 is inserted firmly in a copper socket 12 to provide a good heat conduction connection. The copper socket 12 likewise has a substantially cylindrical shape of about double the diameter of platinum electrode 11 with an axial boring to receive the platinum electrode. On the face opposite the axial boring for receiving the platinum electrodes is a second axial boring a smaller diameter which leads to the vicinity of the platinum electrode 11. This second axial boring serves to receive a temperature measuring element 14, for example a thermistor, and its lead 17.

Figure 3:
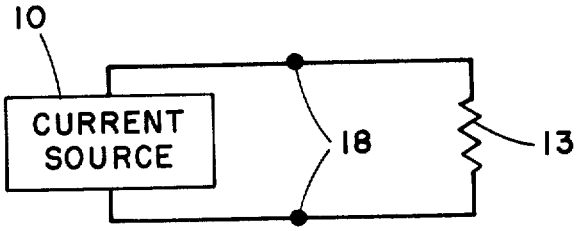
FIG. 3 shows a schematic electrical circuit of the heating winding connection to a current source.

The outer surface of the copper socket 12 is interrupted by an encircling, broad recess about which is wound a heating winding 13, for example, a resistance wire. The lead 18 to the heating winding is passed from end-face of the copper socket 12 through an eccentric boring to a suitable current source 10 as is illustrated in FIG. 3. A lead 16 for the electrode current is attached in a further eccentric boring. The whole arrangement is enclosed by a substantially cylindrical capsule 15 of a plastic (e.g. of PVC, nylon) which only leaves free the tip of the platinum electrode 11 and, on the opposite face, the lead wires 16, 17, 18, which are expediently incorporated into a single cable.

Figure 2:
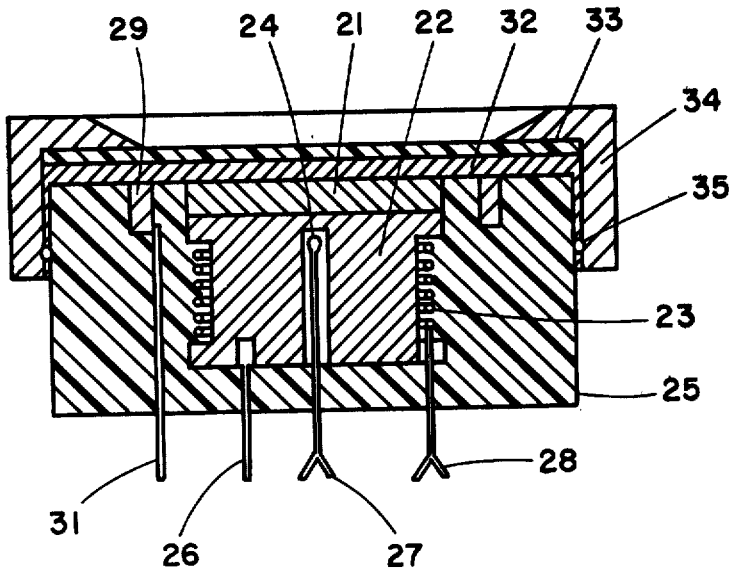
FIG. 2 shows a section through another embodiment of an electrode arrangement according to the invention, for partial pressure measurements.

Another embodiment is illustrated in FIG. 2, which is especially suitable for quantitative partial pressure measurements of $O_2$, $H_2$ etc. on the skin. Here a disc-shaped platinum electrode 21 is in heat-conducting contact with a substantially cylindrical copper block 22 of the same diameter as platinum electrode 21. The outer surface of the copper block 22 is provided with an encircling recess in which is located at heating winding 23. The lead 28 to the heating winding passs through a boring which connects the end-face of the copper block 22 opposite the platinum electrode 21 with the encircling recess. A further eccentrically disposed boring in this end-face serves for the attachment of the lead 26 for the electrode current. In addition, directed from the same face of the copper block into the vicinity of the platinum electrode 21 is an axial boring in which is located a temperature-measuring element 24 with the leads 27.

A silver ring 29, serving as a reference electrode, is chlorinated on one of its flat faces and displays an internal diameter which is greater than the diameter of the platinum electrode. It is so arranged that its entire chlorinated face lies in a common plane with the outer exposed face of the platinum electrode 21. A lead 31 is directed to the back face of the silver ring and is combined with the leads 26, 27, 28 into a single cable. The whole arrangement is enclosed with a smoothly cylindrical capsule 25 of a suitable plastic (for example, PVC, nylon, etc.). As depicted, one end-face of the capsule 25 lies in the plane defined by platinum electrode 22 and silver ring 29, leaving exposed their surfaces. The whole end-face, including the platinum and AgCl surface, is coated with an electrolyte film 32 and thereover covered with a suitable membrane 33 (e.g. teflon). This member 33, serving as the application or skin contact surface of the electrode arrangement, is secured by a substantially annular capsule 34. In order to exclude the access of gas from outside, the gap between the two capsules 25 and 34 is sealed off by an O-ring 35 which is fitted in corresponding ring grooves.

It has been found that heating up of the skin, in the region of the measuring electrode, to about 40°–42° C. is reasonable. A markedly higher temperature is, as a rule, not admissible because of the skin lesions caused by it. In operation, the heating spiral is provided with a current the strength of which is regulated with the aid of the temperature-measuring element. Any known temperature-regulation circuit 20 is suitable for this purpose, as long as it is sufficiently sensitive.

The electrode in accordance with the invention is particularly advantageous since it makes possible a hyperaemization in the region of the tissue and the skin in which the measurement is undertaken without additional preparations having to be applied. This is particularly useful when it is desired to measure certain positions of the body surface where the application of hyperaemizing preparations is problematical. Such an electrode is also expedient in the case of mass investigations.

An additional advantage of the electrode is the considerable stabilization of the electrode reaction, to provide a measurement in a standarized environment as the influence of fluctuations of the ambient temperature, i.e. both of the surrounding air and of the skin, is eliminated.

We claim:

1. An electrode arrangement for application to a body surface for bloodless measurement in connection with the concentration or the partial pressure of a gas in the blood [including] *comprising*, sensor means for *electrochemically* deriving, in vivo, electrical signals indicative of the *concentration or* partial pressure of gas in *the* blood [and having] , *said sensor means including* a face member [adapted] for body contact[, the improvement comprising:]*; and* heating means in direct thermal contact with [said sensor means and adapted to transmit to said face member a thermal condition for thermal stimulation at the applied body surface of local blood circulation] *the face member for transmitting heat throughout the face member into the body tissue directly therebeneath to produce a condition of sufficient hyperemia in said body tissue.*

2. An electrode arrangement according to claim 1 whereby said heating means includes a current source and a resistance winding connected from said current source.

3. An electrode arrangement according to claim 2 whereby said heating means also includes:

thermally conductive block means positioned in thermal contact with said sensor means and said winding being mounted on said block means.

4. An electrode arrangement according to claim 3 whereby said face member is of a material adapted for catalysing the electrochemical reaction at the body surface to which applied.

5. An electrode arrangement according to claim 4 whereby the face member of said sensor means is of platinum.

6. An electrode arrangement according to claim 3 whereby said sensor means further includes at said face member a cover membrane, permeable for the gas to be measured.

7. An electrode arrangement according to claim 1, whereby said heating means includes: temperature regulating means having a temperature-measuring element the measuring probe of which is mounted in the vicinity of said sensor means.

8. An electrode arrangement for application to a body surface for bloodless measurement in connection with the concentration or the partial pressure of a gas in the blood comprising:

a substantially cylindrical electrically and heat conductive member provided with an encircling recess about its outer surface and a first axial boring on one end-face;

smoothly cylindrical electrode means lying on the member end-face opposite said boring and electrically and heat-conductively coupled with said member;

heating winding means mounted in said recess for generating a thermal condition for application to said body surface;

temperature measuring means mounted in said axial boring;

annular reference electrode means mounted concentrically with the electrode means;

a contact face of said reference electrode lying in a common plane with the end-face of the electrode means distal to said member;

an electrolyte film covering the contact face and the end-face of the electrode means;

membrane means covering said electrolyte film, adapted for body contact; and lead means electrically coupled with said electrode means for deriving in vivo electrical signals indicative of the partial pressure of gas in blood.

* * * * *